(12) United States Patent
Hogan

(10) Patent No.: US 7,010,352 B2
(45) Date of Patent: Mar. 7, 2006

(54) TRANSCUTANEOUS ELECTRICAL NERVE LOCATOR

(75) Inventor: Quinn H. Hogan, Whitefish Bay, WI (US)

(73) Assignee: The MCW Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 10/731,273

(22) Filed: Dec. 9, 2003

(65) Prior Publication Data

US 2004/0138584 A1    Jul. 15, 2004

Related U.S. Application Data

(60) Provisional application No. 60/432,407, filed on Dec. 11, 2002.

(51) Int. Cl.
*A61N 1/18* (2006.01)
(52) U.S. Cl. ............... 607/48; 600/547; 600/554; 607/115; 607/145
(58) Field of Classification Search ........... 600/554, 600/587, 486, 557, 547, 300, 309, 306, 308, 600/344, 384, 388, 393, 503; 607/46, 48, 607/115, 145; 2/161.7; 604/116
See application file for complete search history.

(56) References Cited

U.S. PATENT DOCUMENTS

| | | | | |
|---|---|---|---|---|
| 3,191,824 A | * | 6/1965 | Burr ........................ | 223/101 |
| 4,510,939 A | | 4/1985 | Brenman et al. | |
| 4,515,168 A | * | 5/1985 | Chester et al. ............ | 600/554 |
| 4,616,660 A | | 10/1986 | Johns | |
| 4,962,766 A | | 10/1990 | Herzon | |
| 5,070,862 A | * | 12/1991 | Berlant .................... | 601/21 |
| 5,284,153 A | * | 2/1994 | Raymond et al. .......... | 600/554 |
| 5,830,151 A | * | 11/1998 | Hadzic et al. ............. | 600/554 |
| 6,098,854 A | * | 8/2000 | Apple ....................... | 223/101 |
| 6,162,185 A | * | 12/2000 | Amano et al. ............. | 600/557 |
| 6,299,586 B1 | * | 10/2001 | Cao ......................... | 601/134 |
| 6,533,732 B1 | * | 3/2003 | Urmey ...................... | 600/554 |
| 6,595,918 B1 | * | 7/2003 | Gopinathan et al. ....... | 600/300 |
| 2002/0095080 A1 | | 7/2002 | Cory et al. | |

OTHER PUBLICATIONS

Use of Transcutaneous Nerve Stimulation to Assist Interscalene Block; ANESTH ANALG 1993;76:902-20; Michael F. Roizen, MD.

Upper Extremity Blocks; Regional Anesthesia and Analgesia 20(2): 100-104, 1995; J. Shannon, MD, et al.

Anesthesia Technique, A New Technique of Continuous Interscalene Nerve Block; Canadian Journal of Anesth 1999/ 46:3/pp. 275-281; Andre P. Boezaart, et al.

Surface Mapping Of Peripheral Nerves In Children With A Nerve Stimulator, Blackwell Science LTD, Paediatric Anaesthesia 2002/12:298-403; A.T. Bosenberg, et al.

Percutaneous Electrode Guidance: A Noninvasive Technique For Prelocation of Peripheral Nerves To Facilitate Peripheral Plexus or Nerve Block; Regional Anesthesia and Pain Medicine, vol. 27, No 3 (May-Jun.), 2002: pp. 261-267; William F. Urmey, MD et al.

* cited by examiner

*Primary Examiner*—Jeffrey R. Jastrzab
(74) *Attorney, Agent, or Firm*—Quarles & Brady LLP

(57) ABSTRACT

A conductive electrode is attached to the clinician's finger and current pulses are applied thereto as the clinician searches for a nerve to be anesthetized by palpating in the region of the nerve. The target nerve is stimulated to indicate when the nerve is located.

3 Claims, 1 Drawing Sheet

TRANSCUTANEOUS ELECTRICAL NERVE LOCATOR

CROSS-REFERENCE TO RELATED APPLICATIONS

This application is based on U.S. Provisional Patent Application Ser. No. 60/432,407 filed on Dec. 11, 2002 and entitled "Transcutaneous Electrical Nerve Locator."

BACKGROUND OF THE INVENTION

Peripheral nerve blockade provides anesthesia of a region of the body by applying local anesthetic to a selected nerve or plexus of nerves. Growing popularity of this technique is due to its safety relative to general anesthesia, suitability for outpatient surgical care, and the prolonged postoperative pain relief it provides.

The main technical challenge for safe and effective peripheral nerve blockade is the placement of a needle close to the target nerve without entering the nerve, for the purpose of injecting a volume of anesthetic solution. Identification of the proper site for injection involves two sequential phases. First, the place for needle puncture of the skin must be determined. Secondly, the needle must be advanced in the proper direction and to the proper depth prior to injection. The skin puncture site is typically determined by identifying relevant landmarks using visual examination and palpation through the skin. These landmarks include contours of muscles and bones, and arterial pulses. The second phase of needle insertion uses a different repertoire of techniques for perfecting the placement of the needle. Contact with bones or vessels is used when these landmarks are known to be close to the target nerve. Alternatively, needle contact with the nerve may be sought, in which case the provoked sensation confirms needle placement. Finally, current may be passed through the needle to stimulate the nerve electrically. This creates a radiating sensation and contraction of the muscles innervated by the stimulated nerve. In most cases, this final technique, electrical nerve stimulation, is used for final needle placement.

While the techniques above are widely used, success is highly variable. For instance, a 20% failure rate is typical for brachial plexus blockade even after substantial experience is acquired (Konrad 1998). Because nerve stimulation through the needle is a highly reliable method of needle identification, the current limitation is the first phase of the process, namely choosing the correct initial needle puncture site. Human anatomy is highly variable, such that nerves and the structural landmarks used to find them are not consistently placed. Additional challenges are faced when the subject is large or if injury has distorted structure. Since the needle, once inserted, can be used to search a zone only about a 1 cm wide, many failures are do to the initial placement of the needle puncture through the skin at a site too distant from the nerve. In addition to pain and discomfort, damage to various organs may ensue.

The remedy for the limitations discussed above is improved identification of the optimal needle insertion site. If this can be specified within 1 cm or less, the well-established methods for directing needle manipulation, particularly electrical stimulation through the needle, can be used with high success.

Stimulation for the purpose of identifying the location of a nerve for blockade has been proposed in published papers. In one case [Bosenberg et al, Paedriatric Anaesthesia 2002, 12:398–403], application of current to the skin to map the nerve is done prior to cleaning the skin for puncture and is not compatible with simultaneous palpation or compression with the nondominant hand. In another publication [Urmey et al, Regional Anesthesia and Pain Medicine 2002, 27:261–7], a device is described that stimulates transcutaneously and through which the injection needle is passed. This method prevents the use of the nondominant hand for any purpose other than holding the stimulating device against the skin by its handle.

SUMMARY OF THE INVENTION

Stimulation of the nerve through the skin is a method that would allow accurate location of the nerve provided the identified target area is narrow, there is minimal discomfort, risk is low, and the method is practical. It is desirable, however, for the operator to retain free use of both hands to allow simultaneous palpation and control of tissue movement. The present invention is a device that allows highly accurate specification of the nerve site while still permitting the operator the critical freedom of full use of both hands.

The device includes an electrode having an electrically conductive surface attached to the palpating finger of the clinician and the electrode is connected through a wire to a source of electrical current that can be pulsed at a chosen intensity and frequency. A ground lead is attached to the patient with a self-adhesive EKG patch electrode at a site distant to the needle insertion. The palpation finger is used to search for the target nerve and current pulses are applied through the electrode to stimulate the nerve when it is located.

DETAILED DESCRIPTION OF THE PREFERRED EMBODIMENT

Figure 1:
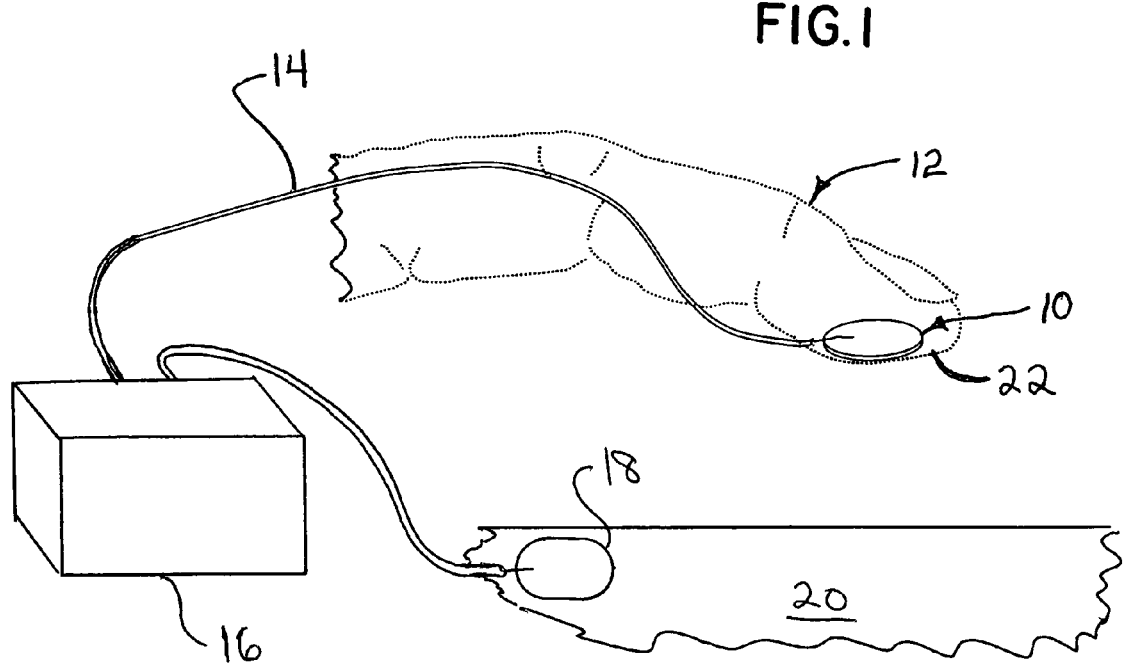
FIG. 1 is a pictorial view of the electrically conductive electrode attached to the palpating finger of the clinician.

Referring particularly to FIG. 1, a contact electrode 10 having an electrically conductive surface is retained to the palpating finger 12 of a clinician. This electrode 10 is connected by means of a wire 14 to a source of current pulses 16. Another electrode 18 attached to the patient 20 at a remote location is also connected to the current source 16 to complete the electrical circuit. In the preferred embodiment, the contact electrode 10 is made from a substantially circular layer of conductive metal having a thickness of 600 micrometers and a diameter of 9 mm. This surface area is important although it can be appreciated that an exact circular shape is not required. A larger contact area does not permit exact location of the nerves, while a smaller contact area intensifies the current density and can produce pain upon delivery of a stimulus adequate to activate the underlying nerve. The edges of the surface of the electrode 10 that is applied to the patient's skin is rounded to avoid skin abrasion, and an electrical lead is attached on the aspect away from the patient.

The device is employed by mounting it on the operator's finger in such a location that it is flatly apposed to the patient's skin when the operator's finger 12 is pressed against the patient 20. Since the usual posture of the fingers during palpation for identifying landmarks is slightly arched, the optimal contact of the electrode 10 to the patient 20 is achieved when the electrode is mounted on the operator's distal finger pad 22. In this embodiment, this is achieved with a double-stick adhesive membrane between the electrode and operator's gloved finger 12, typically the middle or index finger. The wire lead 14 is attached along the back of the operator's finger 12 and hand.

The operator uses his hands in the customary way. Specifically, the nondominant hand seeks landmarks and the dominant hand holds the needle that will be inserted through the chosen site. The sterilized electrode 10, attached to the sterile gloved finger 12 of the clinician's nondominant hand, and it, is pressed gently against the skin in the approximate zone of the target nerve. The current source is started, typically with pulses at 1 second intervals and 5 mA current amplitude. The fingers are moved in such a way that the electrode 10 remains in contact with the same skin site, but this skin (with the electrode) is moved across the deeper structures. Since nerves are located beneath the fascia, they remain substantially stationary as the skin and electrode travel over them.

When adequate current enters the nerve, a distal motor response is noted. The particular movement is characteristic of each nerve, allowing exact identification of the underlying nerve. Maximum motor response is noted as the stimulation site is moved in small increments to either side of the longitudinal path of the nerve, thus identifying the exact site of the nerve. Decreasing current delivery to the stimulating contact allows refinement of the maximal response site. The operator's palpating hand then holds this position fixed while the needle is inserted through the skin. Conventional methods as described above are then employed to perfect the needle direction and depth.

Initial observations demonstrate the efficacy of this method for identification of the following nerves: brachial plexus at the interscalene groove and in the axilla; ulnar, median, radial and musculocutaneous individually in the arm; femoral nerve; common peroneal nerve; sciatic nerve in the popliteal fossa. These are major sites for clinical peripheral nerve blockade. In all cases, stimulation and location was achieved at current levels (1–5 mA) that were not painful. Transcutaneous stimulation of the nerve was achieved without diminishing the ability of the operator to perceive pulses or deep tissue contours with the finger to which the stimulator was attached. A site of maximum motor response was readily evident in a zone approximately 5 mm wide.

The location of the stimulating surface on the operator's finger 12 is an important aspect of this device. Other possible approaches that could be employed for transcutaneous nerve location would involve encumbering the operator's hands. For instance, a cutaneous stimulator through which the needle is passed requires holding such a device with the nondominant hand while the other inserts the needle, such that the nondominant hand can perform no other function. Alternatively, a pen-like cutaneous stimulator held in the dominant hand would have to be put down and replaced in the hand with the needle. The proposed placement of the stimulator contact on the finger permits palpation with the nondominant hand in the customary fashion during transcutaneous nerve location. Immediately upon locating the nerve, the needle can be inserted in the selected site without further manipulations. Maintaining customary use of the nondominant hand in this way serves several critical purposes. 1) Sensing deep structures is an important tactile process that aids in defining the needle insertion site. 2) Additionally, the fingers are used to compress the superficial tissues to shorten the distance from needle to the target nerve. 3) Furthermore, the fingers of the nondominant hand maneuver the skin and stabilize the soft tissue structures while the needle is inserted. 4) Also, the fingers are used to apply pressure to one side of the needle or the other to direct the spread of the injected solution in the opposite direction, away from unintended nerves or structures. 5) Finally, the nature of injectate spread within the tissues can be discerned by palpation with the fingers during injection: accumulation in the superficial (subcutaneous) tissues is undesirable and is sensed as a sausage-shaped mass, whereas injection properly beneath the fascia feels like a broad thickening. When clinicians add electrical nerve location for improving block safety and success, they will reasonably desire to retain the valuable technical components they have used heretofore. Thus it is a feature of the present invention that the nondominant hand remains available to perform these critical functions.

Alternative embodiments of the invention are possible. The contact surface need not be firm metal but could be a foil or spray-on conductive surface. There are also optional methods of attachment of the device to the finger 12. A sterile-packaged unit that is self-adhesive would provide universal compatibility and allow attachment to any finger of any type of glove. Alternatively, gloves could be manufactured with the conductive material built in. This would require stocking many sizes of gloves of both the right and left hand, and different applications may require attachment to the index or middle finger. An intermediate option for attachment would be in the form of a finger cot with the conductive surface and connecting wire attached.

The wire lead 14 from the finger contact surface 10 is restrained from excess movement by a self-adhesive patch 6 inches from the finger, for the purpose of securing the wire to the back of the gloved wrist. This was devised so that the lead 14 may slip through the attaching mechanism to allow flexibility in the placement of the adhesive patch, to accommodate various sized hands or types of gloves.

Improved transcutaneous electrical conduction may be achieved by applying sterile conductive gel to the surface being palpated. The conductive gel is packaged with the stimulation device. Lower current thresholds are achieved this way, thus allowing nerve location with less sensory stimulation.

The invention claimed is:

1. A method for anesthetizing a nerve in a subject, the steps comprising:
    a) placing an electrode on the finger of one hand of the clinician;
    b) palpating the subject with the finger of the one hand of the clinician to locate structures in the vicinity of the nerve;
    c) applying current pulses to the subject through the electrode to locate the nerve by stimulating the nerve; and
    d) injecting an anesthetic into the subject using the other hand of the clinician.

2. An electrode for locating a nerve in a subject during an anesthetizing procedure, the combination comprising:
    a conductive layer having a conductive surface for contacting the subject and a back surface;
    a lead for electrically connecting the conductive layer to a source of current pulses;
    an adhesive layer disposed on the back surface of the conductive layer to enable the back surface of the conductive layer to be removably attached to the distal finger pad of an examining clinician.

3. The electrode as recited in claim 2 in which the conductive surface has a substantially circular shape and has a diameter of substantially 9 mm.

* * * * *